US010758711B2

(12) United States Patent
Vin et al.

(10) Patent No.: US 10,758,711 B2
(45) Date of Patent: Sep. 1, 2020

(54) TREATMENT KIT, ASSOCIATED MEASURING DEVICE AND ASSOCIATED PREPARATION METHOD

(71) Applicant: PEROUSE MEDICAL, Ivry le Temple (FR)

(72) Inventors: Laëtitia Vin, Gisors (FR); Thomas Walter, Rueil Malmaison (FR)

(73) Assignee: PEROUSE MEDICAL, Ivry le Temple (FR)

( * ) Notice: Subject to any disclaimer, the term of this patent is extended or adjusted under 35 U.S.C. 154(b) by 534 days.

(21) Appl. No.: 15/381,395

(22) Filed: Dec. 16, 2016

(65) Prior Publication Data

US 2017/0173305 A1 Jun. 22, 2017

(30) Foreign Application Priority Data

Dec. 18, 2015 (FR) .................................... 15 62850

(51) Int. Cl.
| | |
|---|---|
| *A61M 25/06* | (2006.01) |
| *A61M 25/09* | (2006.01) |
| *A61M 25/01* | (2006.01) |
| *A61B 5/042* | (2006.01) |
| *A61B 5/06* | (2006.01) |
| *A61B 5/00* | (2006.01) |
| *A61M 39/02* | (2006.01) |

(Continued)

(52) U.S. Cl.
CPC ......... *A61M 25/0662* (2013.01); *A61B 5/042* (2013.01); *A61B 5/065* (2013.01); *A61B 5/6852* (2013.01); *A61M 25/01* (2013.01); *A61M 25/09* (2013.01); *A61M 39/0208* (2013.01); *A61B 5/0452* (2013.01); *A61M 2025/0008* (2013.01); *A61M 2025/09133* (2013.01); *A61M 2025/09183* (2013.01)

(58) Field of Classification Search
USPC .................................. 600/508–509; 607/116
See application file for complete search history.

(56) References Cited

U.S. PATENT DOCUMENTS

| | | | |
|---|---|---|---|
| 2003/0144656 A1 | 7/2003 | Ocel et al. | |
| 2005/0000523 A1* | 1/2005 | Beraud ............ | A61B 17/06004 128/885 |
| 2008/0255475 A1 | 10/2008 | Kondrosky et al. | |

(Continued)

FOREIGN PATENT DOCUMENTS

WO  2011/094631 A1  8/2011

OTHER PUBLICATIONS

Search Report for FR Application 1562850 dated Aug. 31, 2016.

*Primary Examiner* — Nicole F Lavert
(74) *Attorney, Agent, or Firm* — Thompson Coburn LLP; Steven M. Ritchey

(57) ABSTRACT

The present invention relates to a treatment kit comprising:
a guide having a distal end and a proximal end;
a position determination device for determining the position of the distal end of the guide in the body of a patient; and
a catheter intended to be inserted into the body of the patient.
The guide is graduated between its distal end and its proximal end, the graduations of the guide making it possible to measure a length of insertion of the guide into the body of the patient, and the catheter is adapted so as to be cut to a predetermined length that is determined based on the length of insertion.

20 Claims, 4 Drawing Sheets

(51) Int. Cl.
  *A61M 25/00* (2006.01)
  *A61B 5/0452* (2006.01)

(56) References Cited

U.S. PATENT DOCUMENTS

2012/0277544 A1* 11/2012 Fernandes ......... A61M 25/0102
                                                    600/300
2013/0023758 A1*  1/2013 Fabro ................ A61B 1/00078
                                                    600/424

* cited by examiner

TREATMENT KIT, ASSOCIATED MEASURING DEVICE AND ASSOCIATED PREPARATION METHOD

CROSS-REFERENCE TO RELATED APPLICATIONS

The present application is a non-provisional application claiming the benefit of FR 15 62850, filed Dec. 18, 2015, which is incorporated herein by reference in its entirety.

FIELD OF THE INVENTION

The present invention relates to a treatment kit comprising a guide having a distal end and a proximal end, a position determination device for determining the position of the distal end of the guide in the body of a patient, and a catheter intended to be inserted into the body of the patient.

Such a kit is used, for example, to prepare the placement of a venous access implant, such as an implantable port, a peripherally inserted central catheter (PICC), and a central venous catheter (CVC).

BACKGROUND OF INVENTION

It is important to be able to precisely position the implant in the body of the patient. In particular, in the field of vascular implantation, it is desirable to be able to position a catheter in a manner such that its distal end arrives precisely at the junction between the superior vena cava and the right atrium.

It is a known technique to use a guide fitted with an ECG (electrocardiogram) sensor probe implanted in a catheter that insulates the guide. The principle of the ECG technique relies on the fact that the shape and height of the wave P of the ECG is a function of the position of the detection electrode, and varies significantly when this electrode is located at the intersection between the superior vena cava and the right atrium. This position corresponds to the place where the distal end of the implanted catheter must be found. At the time of implantation of the catheter into the body of the patient, the guide in the catheter makes it possible to determine the position of the catheter within the body of the patient. When the catheter is in the desired position, the practitioner measures the length of insertion of the catheter, then removes it and cuts it to the length of insertion measured. The catheter measuring the length of insertion is subsequently reimplanted into the body of the patient.

However, such a method requires a succession of complex steps with multiple successive implantations of the catheter into the body of the patient, which is tedious and time consuming for the practitioner. Furthermore the reimplantation of the catheter increases the risk of infection.

SUMMARY OF INVENTION

An objective of the invention is to offer a treatment kit that provides for a very precise and simple process for placing a catheter in position in a blood vessel and thereby limiting the risk of infections. The degree of precision should preferably be sufficient to ensure that the catheter is positioned at a distance of less than one centimetre from the targeted zone.

To this end, the object of the present invention relates to a kit of the aforementioned type characterised in that the guide is graduated between its distal end and its proximal end, the graduations of the guide making it possible to measure a length of insertion of the guide into the body of the patient, and in that the catheter is adapted so as to be cut to a predetermined length that is determined based on the length of insertion.

The treatment kit according to the invention may comprise one or more of the following characteristic features taken into consideration individually or in accordance with any technically possible combinations:
   the catheter is adapted so as to be inserted into the body of the patient, instead of the guide, after it has been cut;
   the position determination device for determining the position of the distal end of the guide in the body of the patient comprises an electrocardiogram sensor probe connected to the proximal end of the guide, with the signal measured by the probe being dependent on the position of the distal end of the guide;
   the guide includes a central portion between the distal end and the proximal end covered with an electrically insulating material, the distal end and the proximal end being made of an electrically conductive material;
   the external diameter of the guide is less than 1.5 mm, in particular less than 0.9 mm, advantageously less than 0.5 mm, and preferably less than 0.4 mm;
   the catheter has a distal end and a proximal end, and the catheter is adapted so as to be cut at its distal end;
   the catheter has a distal end and a proximal end and the catheter includes an implantable port or the base of a peripherally inserted central catheter or of a central venous catheter connected to its proximal end; and
   the guide includes a core that is at least partially electrically conductive and an insulating external sheath, with the graduations of the guide being arranged over the external sheath or over the core.

The object of the invention also relates to a guide designed to be inserted partially into the body of a patient and to be connected to a position determination device for determining the position of the distal end of the guide in the body of a patient, with the guide having a distal end and a proximal end, characterised in that the guide is graduated between its distal end and its proximal end, the graduations of the guide making it possible to measure from the exterior of the body of the patient a length of insertion of the guide into the body of the patient.

The guide according to the invention may include the following characteristic feature:
   the guide includes a central portion between the distal end and proximal end that is covered with an electrically insulating material, with the distal end and the proximal end being made of an electrically conductive material.

The object of the invention also relates to a measuring device comprising:
   a guide designed to be inserted partially into the body of a patient, with the guide having a distal end and a proximal end;
   a position determination device for determining the position of the distal end of the guide in the body of the patient, that is capable of being connected to the guide;
   characterised in that the guide is graduated between its distal end and its proximal end, the graduations of the guide making it possible to measure a length of insertion.

The object of the invention also relates to a use for a length of insertion previously measured outside of the body of the patient by making use of the graduations of the guide of a measuring device as described here above for cutting, outside of the body of the patient, a catheter intended to be inserted into the body of the patient.

The use according to the invention may include one or more of the following characteristic features taken into consideration individually or in accordance with any technically possible combinations:
- the catheter has a distal end and a proximal end, with the catheter being cut at its distal end;
- the proximal end of the catheter is connected to an implantable port or the base of a peripherally inserted central catheter or of a central venous catheter prior to the cutting of the catheter; and
- the catheter is maintained under sterile conditions outside of the body of the patient until it is cut.

The object of the invention also relates to a preparation method for preparing the implantation of a catheter including the following steps:
- provision of a treatment kit as previously described above;
- determination of the position of the distal end of the guide in the body of the patient;
- insertion of the guide up to a desired position;
- measuring of the length of insertion of the guide with the graduations of the guide, from the exterior of the patient's body, with the guide being in a desired position; and
- cutting of the catheter to a length determined on the basis of the measured length of insertion.

The preparation method for preparing the implantation of a catheter according to the invention may include one or more of the following characteristic features taken into consideration individually or in accordance with any technically possible combinations:
- the catheter is kept in sterile conditions until the step of cutting;
- the preparation method for preparing the implantation of a catheter, in addition, includes the following step:
- removing of the guide prior to insertion of the catheter that has been cut;
- the preparation method for preparing the implantation of a catheter, in addition, includes the following step:
  - provision of an introducer that includes a dilator, the guide being adapted to receive the dilator of the introducer, the introducer being adapted to receive the cut catheter;
- placing in position of the introducer by means of the guide in the body of the patient;
- when the guide is in the desired position, the distal end of the guide is located at the junction of the superior vena cava and the right atrium of the patient;
- the determination of the position of the distal end of the guide in the body of the patient includes an electrocardiogram measurement, a modification of the wave P measured during the electrocardiogram indicating the positioning of the guide in the desired position.

BRIEF DESCRIPTION OF THE DRAWINGS

The invention will be better understood upon reading the description which follows, given purely by way of example, and with reference made to the accompanying drawings.

DETAILED DESCRIPTION OF INVENTION

Figure 1:
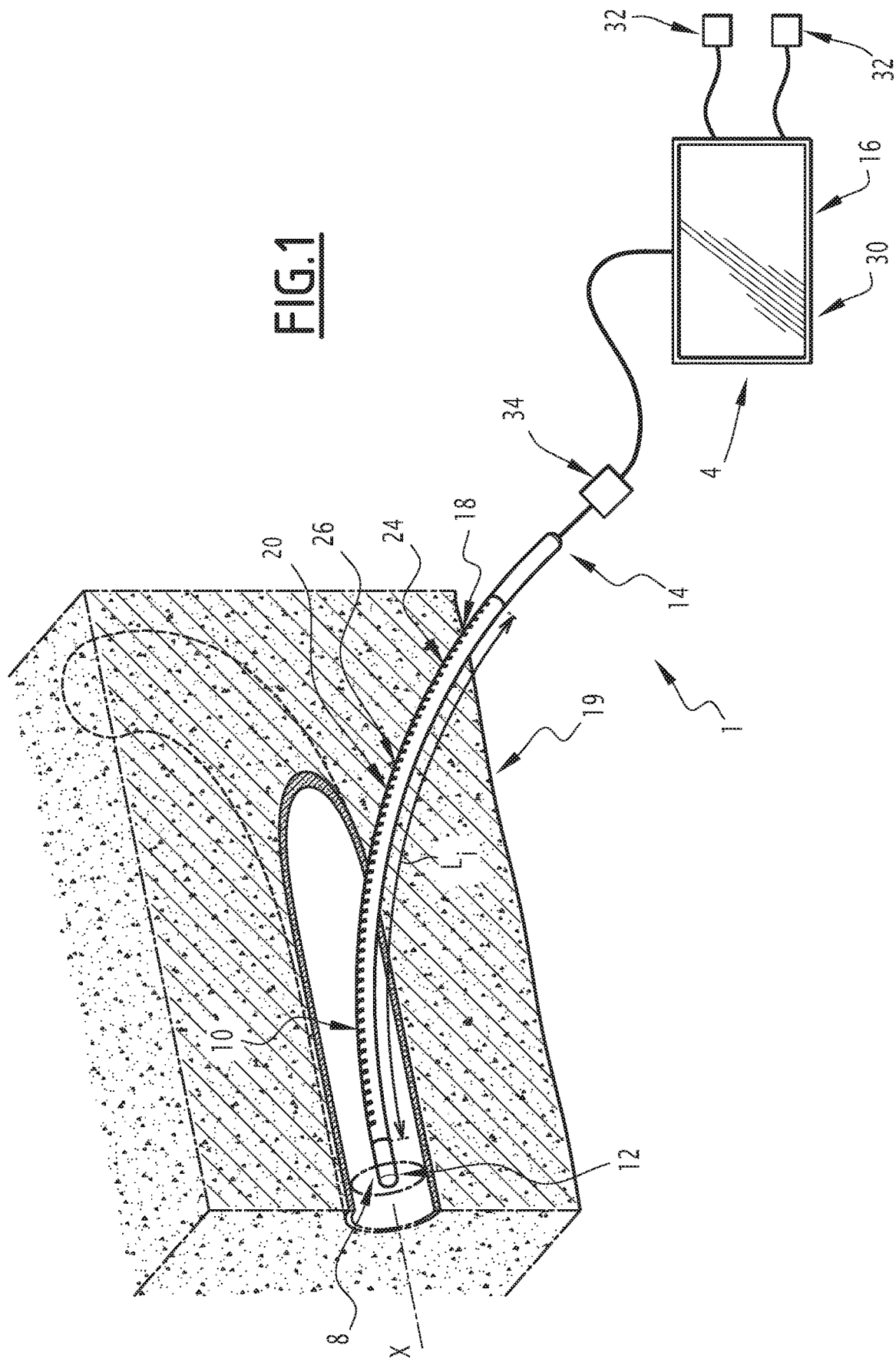
FIG. 1 is a schematic view of a measuring device of a treatment kit according to the invention, introduced partly into the body of a patient.

A treatment kit 1 intended for treating a patient is illustrated in FIGS. 1 to 4. The treatment kit 1 comprises a measuring device 4 and a catheter 6 intended to be inserted into the body of a patient.

In particular, the catheter 6 is intended to be inserted into the blood system, especially at the level of a zone to be treated 8. The zone to be treated 8 is for example in the venous system, in particular at the junction between the right atrium and the superior vena cava of the patient.

The measuring device 4 comprises a guide 10 having a distal end 12 that is intended to be introduced into the patient and a proximal end 14 that is intended to remain outside the patient's body, and a position determination device 16 for determining the position of the distal end 12 of the guide 10 in the body of the patient.

Advantageously, the treatment kit 1 comprises, in addition, a puncture needle and an introducer that is not shown. Advantageously, the puncture needle and the introducer used are the same as those known in the state of the art.

The puncture needle defines an internal lumen having an internal diameter that is appropriate to the treatment planned. It is capable of creating a puncture 18 in the skin of the patient and of allowing the insertion of the guide 10 in the body of the patient in the proximity of the zone to be treated 8 from the puncture 18. The puncture 18 goes through the skin 19 of patient and opens into a vein, for example.

The introducer defines an internal lumen having an internal diameter that is appropriate to the treatment planned. The introducer is adapted to receive the catheter 6 that has been cut. In addition, the introducer is adapted to be placed on the guide 10. The introducer comprises a dilator.

The guide 10 is elongated between its distal end 12 and its proximal end 14 along a longitudinal direction X. The length of the guide 10 is greater than or equal to the distance between the position of the puncture 18 and the position of the zone to be treated 8. For example, the length of the guide 10 is greater than or equal to 60 cm.

The external diameter of the guide 10, measured transversely to the longitudinal direction X, is strictly less than the internal diameter of the puncture needle. In addition, the external diameter of the guide 10 is strictly less than the internal diameter of the introducer. Advantageously, the external diameter of the guide 10 is less than 0.9 mm.

In practice for a treatment kit 1 intended for the implantation of an implantable port or a central venous catheter, denoted by the abbreviation CVC, for an adult, the external diameter of the guide 10 is less than or equal to 0.89 mm. For a treatment kit 1 intended for the implantation of an implantable port for a child, the external diameter of the guide 10 is less than or equal to 0.46 mm. For a treatment kit 1 intended for the implantation of a PICC for an adult, the external diameter of the guide 10 is less than or equal to 0.46 mm. For a treatment kit 1 intended for the implantation of a PICC for a child, the external diameter of the guide 10 is less than or equal to 0.36 mm.

The guide 10 includes a central portion 20 between the distal end 12 and the proximal end 14. The central portion 20 is covered with an electrically insulating material.

The guide 10 comprises a core 22 made of an electrically conductive material, for example metal. The core 22 is elongated along the longitudinal direction X. For example, the core 22 comprises an internal frame member 25 and a spring 23 covering the frame member 25. The spring 23 provides flexibility to the core 22.

The guide 10 comprises an external sheath 24 that covers the core 22 over the central portion 20. The external sheath 24 is made of an electrically insulating material. For example, the external sheath 24 is made of plastic and comprises polytetrafluoroethylene (PTFE) or another insulating material.

The guide 10 is graduated between its distal end 12 and its proximal end 14. The graduations 26 of the guide 10 are visible from the external surface of the guide 10 and provide the means for measuring a length of insertion $L_i$ of the guide 10 into the body of the patient.

In the example, the graduations of the guide 10 are arranged on the external sheath 24. By way of a variant, the graduations 26 of the guide 10 are arranged on the core 22 of the guide 10 and the external sheath 24 is transparent.

The graduations 26 of the guide 10 are evenly distributed along the longitudinal direction X of the guide 10. For example, the graduations 26 of the guide 10 are distributed at intervals of one centimetre. By way of a variant, the graduations 26 of the guide are distributed at intervals of half a centimetre.

The external surface of the guide 10 at the distal end 12 and the proximal end 14 is electrically conductive. The distal end 12 and proximal end 14 of the guide 10 are not covered by the insulating sheath 24. The distal end 12 and the proximal end 14 are made of electrically conductive material, for example of the same material as the core. For example, the distal end 12 and the proximal end 14 are covered with a conductive coating.

When the guide 10 is in the body of the patient, the distal end 12 of the guide 10 is thus capable of picking up the electric potential in the vicinity of its position. The core 22 allows for the transmission of this potential to the proximal end 14 of the guide 10. The external insulating sheath 24 prevents the pollution of the potential picked up during the transmission to the proximal end of the guide 10.

The position determination device 16 is capable of determining the position of the distal end 12 of the guide 10 in the body of a patient. The position determination device 16 for determining the position of the distal end 12 is in the example an electrocardiogram device referred to by the abbreviation ECG. The position determination device 16 for determining the position of the distal end 12 of the guide 10 includes a monitor 30, at least one reference electrode 32 and one electrocardiogram sensor 34.

Each reference electrode 32 is capable of picking up an electrical potential at a distance away from the zone to be treated 8. Each reference electrode is intended to be placed away from the puncture 18 on the skin 19 of the patient. In the example, the position determination device 16 comprises two reference electrodes 32 intended to be placed away from the puncture 18 on the skin 19 of the patient.

The electrocardiogram sensor 34 of the position determination device 16 is electrically connected to the proximal end 14 of the guide 10. The electrocardiogram sensor 34 is capable of measuring a signal that is measured depending on the position of the distal end 12 of the guide 10.

The proximal end 14 of the guide 10, that is made of an electrically conductive material is connected to the sensor probe 34 for example by means of a clamp. By way of a variant, the central portion 20 of the guide 10 is wound in a decoiler reel and the proximal end 16 of the guide 10 is connected to the sensor probe by an electrode that is in contact with physiologic serum (saline solution) placed in the decoiler reel of the guide 10.

Figure 4:
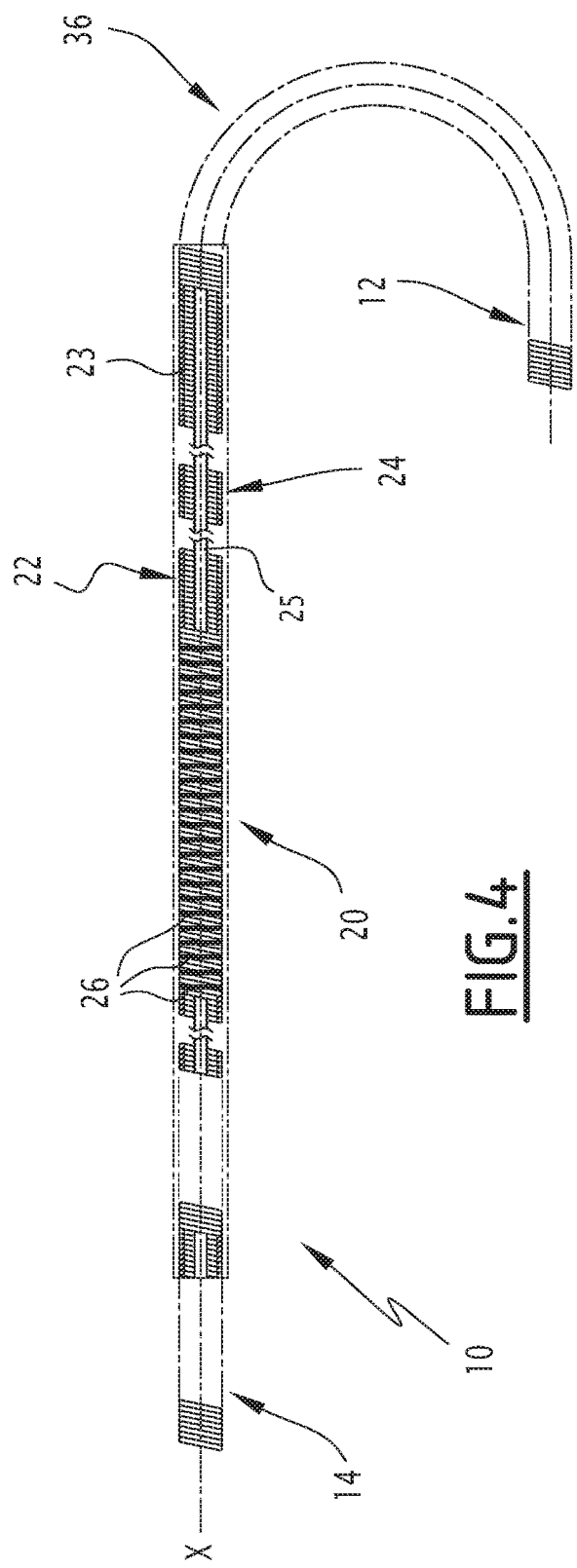
FIG. 4 is a partially exploded view of an example of a guide.

In the example shown in FIG. 4, in the vicinity of the distal end 12 of the guide 10, the guide 10 has a curvature 36. The radius of curvature R is for example equal to 3 mm. This curvature 36 facilitates the moving of the guide 10 in the vein. The central portion 20 that is insulated by the sheath 24 is on the rectilinear section before the curvature 36. The proximal end 14 that is not insulated by the sheath measures for example 2 cm. The distal end 12 that is not insulated by the sheath 24 includes the zone of the curvature 36.

The monitor 30 is capable of displaying an electrocardiogram measurement from the signals picked up by the sensor probe 34 and/or the reference electrodes 32. Furthermore advantageously, the monitor 30 is capable of determining the shape and height of the wave P from the measurement.

Figure 2:
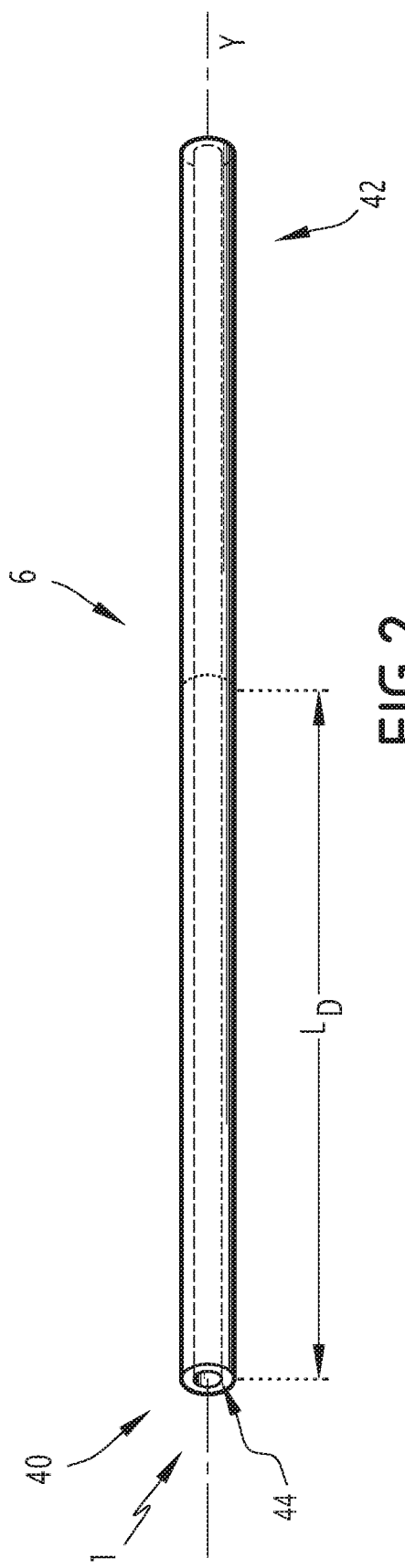
FIG. 2 is a view of the catheter of the treatment kit prior to the cutting thereof.
Figure 3:
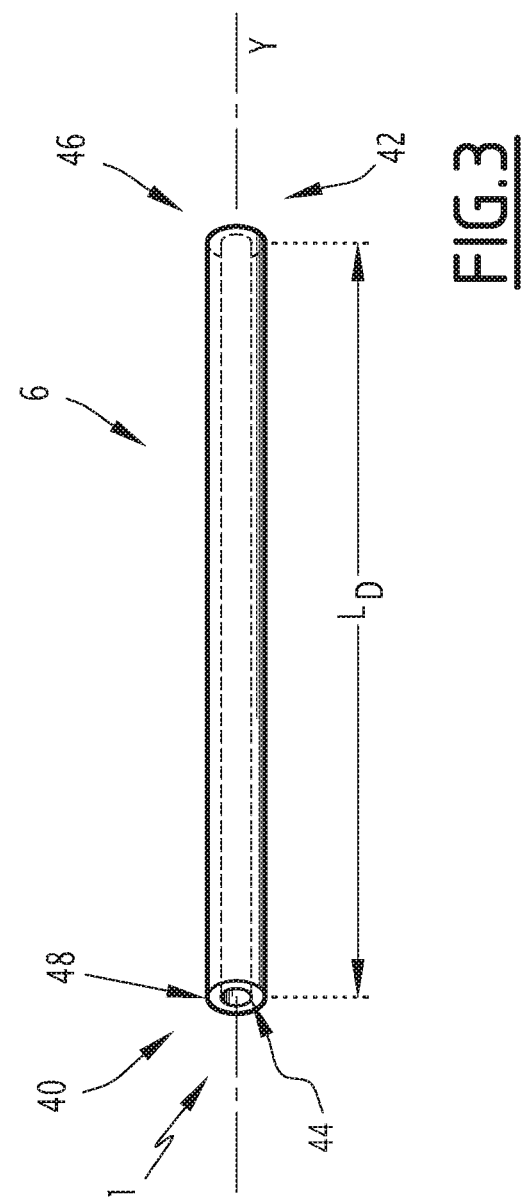
FIG. 3 is a view of the catheter of the treatment kit after it has been cut.

The catheter 6 is shown in FIG. 2 prior to its being cutting and in FIG. 3 after it has been cut.

The catheter 6 is intended to be inserted into the body of the patient. The catheter 6 includes a proximal end 40 and a distal end 42.

The catheter is elongated between its distal end 42 and its proximal end 40 along a direction of elongation Y.

The catheter 6 generally has a length that is greater than 40 cm and comprised between 50 cm and 80 cm. It has a diameter comprised between 1 mm and 5 mm.

The catheter 6 has an internal lumen 44 that is extended along the direction of elongation Y and opening out through the distal end 42 and through the proximal end 40 of the catheter 6.

The diameter of the internal lumen 44, measured transversely to the axis of elongation Y, of the catheter 6 is appropriate to the treatment planned. For example the diameter of the internal lumen 44 of the catheter 6 is comprised between 0.5 mm and 2 mm.

In another variant, the catheter 6 has a plurality of internal lumen 44, for example two or three internal lumen 44, extended along the direction of elongation Y and opening out through the distal end 42 and through the proximal end 40 of the catheter 6.

The catheter 6 is adapted so as to be inserted into the body of the patient, instead of the guide 10, in particular after it has been cut.

In particular, the catheter 6 is adapted, for example, to be inserted into the introducer. Thus, the external diameter of the catheter 6, measured transversely to the axis of elongation Y, is less than the internal diameter of the introducer.

The catheter 6 is adapted so as to be cut at its distal end 42. By way of a variant or additionally, 6 the catheter is adapted so as to be cut at its proximal end 40.

The catheter 6 is adapted so as to be cut to a predetermined length $L_D$ based on the length of insertion $L_i$ of the guide 10.

After being cut, one of either the distal end 42 or the proximal end 40 of the catheter has been truncated. The catheter thus has a truncated end 46 and a non-truncated end 48. The internal lumen 44 of the catheter emerges through the truncated end 46 and through the non-truncated end 48. By way of a variant, the two ends of the catheter 6 are both truncated. In the example represented in FIG. 3, the catheter 6 is cut at its distal end 42. The distance between the two ends 46, 48 of the catheter after it has been cut is equal to the predetermined length $L_D$ determined based on the length of insertion $L_i$ of the guide 10.

Figure 5:
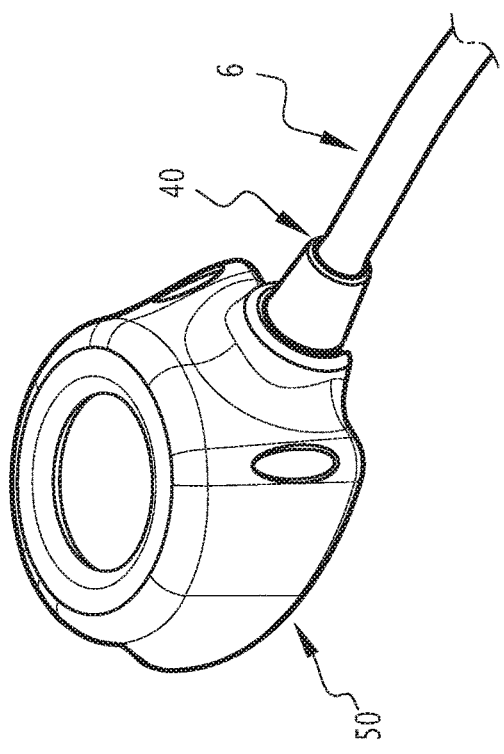
FIG. 5 is a partial view of a catheter connected to an implantable port.

In one example illustrated in FIG. 5, the catheter 6 has, in addition, an implantable port 50 connected to its proximal end 40. The internal lumen 44 of the catheter 6 opens out into the implantable port 50.

In another variant, the proximal end 40 of the catheter 6 is connected to the base of a peripherally inserted central catheter referred to by the acronym "PICC".

In another variant, the proximal end 40 of the catheter 6 is connected to the base of a central venous catheter referred to by the abbreviation "CVC". The functioning of the treatment kit 1 according to the invention will now be described with reference made to FIGS. 1 to 3.

The treatment kit 1 is provided. A puncture 18, for example a venipuncture is performed, for example, by means of the puncture needle.

The reference electrodes 32 are placed at a distance from the puncture 18 on the body of the patient.

Once the venipunctures 18 have been made, the guide 10 is introduced into the puncture needle through its distal end 12 without introducing the catheter 6. The guide 10 travels through the vein from the puncture needle. The guide 10 is moved in the puncture needle and into the vein by the operator.

The position of the distal end 12 of the guide 10, in the body of the patient is determined using the position determining device. For example, the determination of the position of the distal end 12 is effectively carried out continuously during the moving of the guide 10.

The determination of the position of the distal end 12 of the guide 10 in the body of the patient includes an electrocardiogram measurement. For example, the operator checks the shape of the wave P recorded on the monitor 30.

The guide 10 is inserted up to a desired position. For example, when the guide 10 is in the desired position, the distal end of the guide 10 is located at the junction of the superior vena cava and the right atrium of the patient. A modification in the wave P measured in the electrocardiogram indicates the positioning of the guide 10 in the desired position. As soon as the shape of the wave P on the monitor changes abruptly while moving the guide 10, the operator stops moving the guide 10.

When the guide 10 is in the desired position, the length of insertion $L_i$ of the guide 10 is thus measured from outside the body of the patient by making use of the graduations 26 of the guide 10 of the measuring device 4.

The length of insertion $L_i$ of the guide 10 is established by measuring on the exterior of the patient's body from the puncture 18, the graduations 26 of the guide 10 that are visible outside the patient's body between the puncture 18 and the proximal end 14 of the guide 10.

The use of the length of insertion $L_i$ measured previously for the cutting, from outside the body of the patient, a catheter 6 intended to be inserted into the body of the patient will now be described.

The catheter 6 is maintained under sterile conditions outside the body of the patient up to its being cut.

A length of cut $L_D$ of the catheter is determined by the operator from length of insertion $L_i$ previously measured depending on the characteristics of the planned treatment.

For example, the determined cut length $L_D$ is equal to the length of insertion $L_i$. Thus, if the catheter 6 is placed instead of the guide 10, its proximal end 40 will be at the level of the puncture 18 and its distal end 42 will be in the desired position on the zone to be treated 8.

By way of a variant, the predetermined cut length $L_D$ is equal to the sum of the length of insertion $L_i$ and a predetermined length such that the proximal end 40 of the catheter 6 extends beyond the body of the patient from the puncture 18, for example, in order to facilitate the manipulations done by the operator.

By way of a variant, the predetermined cut length $L_D$ is equal to the difference between the length of insertion $L_i$ and a predetermined length, for example, in order for the catheter 6 to be connected to an implantable port 50 under the puncture 18.

The catheter 6 is cut to the cut length $L_D$ determined on the basis of the length of insertion $L_i$ measured.

The catheter 6 is, for example, cut at its distal end 42. Thus the proximal end 40 of the catheter 6 may be connected to an implantable port 50 before the cutting of the catheter 6, as shown by FIG. 5.

It is thus possible to have implantable ports 50 pre-assembled on catheters 6 of standard length, and to cut the distal end 42 of the catheter 6, while also maintaining the implantable port 50 connected. This greatly simplifies the work of the practitioner and ensures a robust connection between the implantable port 50 and the catheter 6.

By way of a variant, the catheter 6 is cut at its proximal end 40.

The operator removes the puncture needle while leaving the guide 10 in position.

The introducer is set in place by means of the guide 10 in the body of the patient. When the introducer is being set in place, the introducer is positioned in a manner such that the guide 10 is in the lumen of the introducer. The introducer moves while following the guide until the desired position is reached.

In addition, the guide 10 is removed from the body of the patient from the puncture 18 by the operator prior to insertion of the cut catheter 6.

Advantageously, the reference electrodes 32 are left on the body of the patient and the sensor probe 34 is disconnected from the guide 10 and then positioned on the body of the patient. This allows for the operator to continue the operation with a standard electrocardiogram monitoring.

The operator removes the dilator from the introducer.

After cutting of the catheter 6, the operator sets the catheter 6 in place in the introducer by inserting the distal end 42 of the catheter 6 in the introducer. The catheter 6 travels in the introducer, up to the vicinity of the zone to be treated 8. As the catheter 6 precisely measures the predetermined length $L_D$, the introduction of the cut catheter 6 allows for the installing in place thereof in a manner such that its distal end 42 is positioned in the desired position.

The operator then withdraws the introducer while leaving the catheter 6 in position.

The invention therefore makes it possible to obtain a treatment kit 1 that is used to ensure the installing in place in a greatly simplified manner of the catheter 6 in the desired position while also limiting the risk of infections.

The preparation of the catheter 6 is a process that is quick to carry out. In addition, it requires less handling action than the methods known in the state of the art since it is not necessary for the catheter 6 to be implanted multiple times.

Furthermore the risk of infection is thus reduced because the catheter 6 is implanted only once in the body of the patient. It can remain under sterile conditions until such time as it is implanted.

In addition, with the catheter 6 precisely measuring the predetermined length $L_D$, when it is set in place, the operator does not need to perform any compensating adjustments by increasing the length of the emerged or visible portion of the catheter. Such compensating adjustments induce the need for more delicate handling of the catheter and thereby increase the risk of infection. In addition, with the measuring and the cutting being precise, the catheter 6 may be set in position at a distance of less than one centimetre from the target zone.

Figure 6:
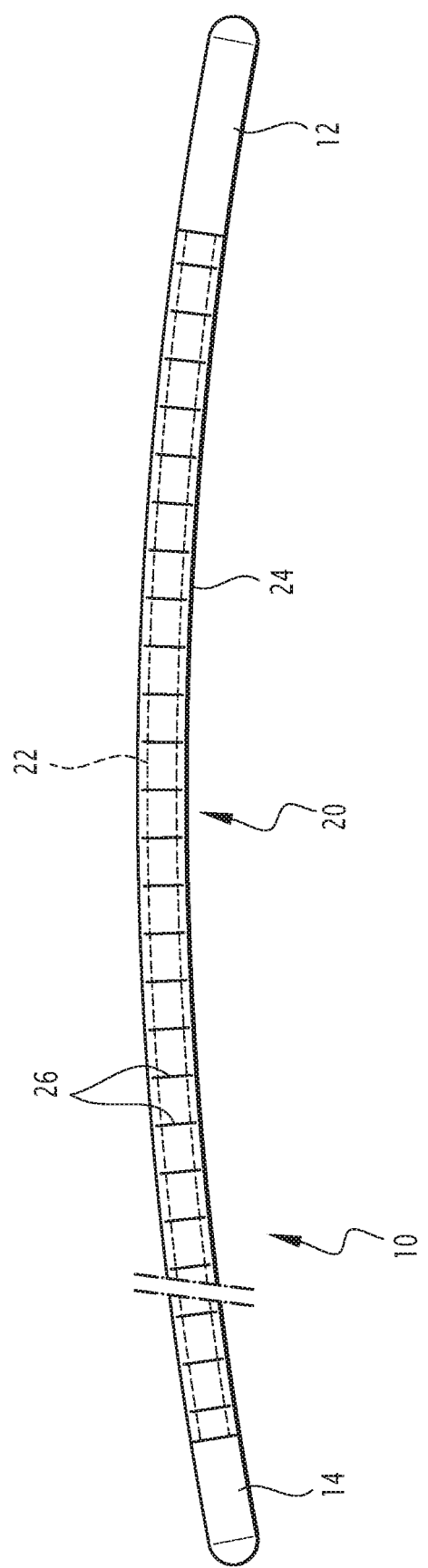
FIG. 6 is a side view of another example of a guide.

In one variant illustrated in FIG. 6, the guide 10 does not present any curvature 36. In addition, the core 22 does not comprise any spring 23. The core 22 is a metal rod. The core 22 has an elongated cylindrical shaped form. The portions of the core 22 at the level of the distal end 12 and proximal end 14 are not covered by the insulating sheath 24. They measure approximately 1 to 2 centimetres.

Such a guide is advantageously designed for the placement of a peripherally inserted central catheter (PICC)

The treatment kit 1 is an apparatus dedicated to the preparation of the installing in place of the catheter. The overall dimensions and nature of the guide 10 may therefore be particularly suitable for this application and hence supported by a CE marking.

In addition, the possibility of cutting the catheter 6 at its distal end 42 and not the proximal end 40, makes it possible to use this technique with pre-connected ports, PICCs, and CVCs, which thereby promotes asepsis and makes the task easier for practitioners and enhances the precision of the positioning of the distal end 42 of the catheter 6.

What is claimed is:

1. A treatment kit comprising:
a guide having a distal end and a proximal end;
a position determination device for determining the position of the distal end of the guide in the body of a patient; and
a catheter intended to be inserted into the body of the patient;
wherein (i) the guide is graduated between the distal end and the proximal end and includes a central portion between the distal end and the proximal end covered with an electrically insulating material, the distal end and the proximal end being made of an electrically conductive material, (ii) the graduations of the guide make it possible to measure a length of insertion of the guide into the body of the patient, and (iii) the catheter is adapted so as to be cut to a predetermined length that is determined based on the length of insertion.

2. The treatment kit according to claim 1, wherein the catheter is adapted so as to be inserted into the body of the patient, instead of the guide after it has been cut.

3. The treatment kit according to claim 1, wherein the position determination device for determining the position of the distal end of the guide in the body of the patient comprises an electrocardiogram sensor probe connected to the proximal end of the guide with the signal measured by the probe being dependent on the position of the distal end of the guide.

4. The treatment kit according to claim 1, wherein the guide includes a central portion between the distal end and the proximal end covered with an electrically insulating material, the distal end and the proximal end being made of an electrically conductive material.

5. The treatment kit according to claim 1, wherein the external diameter of the guide is less than 1.5 mm.

6. The treatment kit according to claim 1, wherein the external diameter of the guide is less than 0.9 mm.

7. The treatment kit according to claim 1, wherein the external diameter of the guide is less than 0.5 mm.

8. The treatment kit according to claim 1, wherein the external diameter of the guide is less than 0.4 mm.

9. The treatment kit according to claim 1, wherein the catheter has a distal end and a proximal end and the catheter is adapted so as to be cut at its distal end.

10. The treatment kit according to claim 1, wherein the catheter has a distal end and a proximal end and the catheter includes an implantable port or the base of a peripherally inserted central catheter or of a central venous catheter connected to its proximal end.

11. The treatment kit according to claim 1, wherein the guide includes a core that is at least partially electrically conductive and an insulating external sheath, and the graduations of the guide are arranged over the external sheath or over the core.

12. A guide designed to be inserted partially into the body of a patient and to be connected to a position determination device for determining the position of the distal end of the guide in the body of a patient, wherein (i) the guide has a distal end, a proximal end, and a central portion between the distal end and the proximal end that is covered with an electrically insulating material, the distal end and the proximal end being made of an electrically conductive material, and (ii) the guide is graduated between the distal end and the proximal end, the graduations of the guide making it possible to measure from the exterior of the body of the patient a length of insertion of the guide into the body of the patient.

13. The guide according to claim 12, the guide further including a central portion between the distal end and the proximal end that is covered with an electrically insulating material, wherein the distal end and the proximal end being made of an electrically conductive material.

14. A measuring device comprising:
a guide designed to be inserted partially into the body of a patient, with the guide having a distal end and a proximal end; and
a position determination device for determining the position of the distal end of the guide in the body of the patient, that is capable of being connected to the guide;
wherein (i) the guide is graduated between the distal end and the proximal end and includes a central portion between the distal end and the proximal end covered with an electrically insulating material, the distal end and the proximal end being made of an electrically conductive material, and (ii) the graduations of the guide makemaking it possible to measure a length of insertion.

15. A preparation method for preparing the implantation of a catheter including the following steps:
provision of a treatment kit according to claim 1;
determination of the position of the distal end of the guide in the body of the patient;
insertion of the guide up to a desired position;
measuring of the length of insertion of the guide with the graduations of the guide, from the exterior of the patients body, with the guide being in a desired position; and
cutting of the catheter to a length determined on the basis of the measured length of insertion.

16. The preparation method according to claim 15, wherein the catheter is kept in sterile conditions until the step of cutting.

17. The preparation method according to claim 15, further comprising removing of the guide prior to insertion of the catheter that has been cut.

18. The preparation method according to claim 15, further comprising:

provision of an introducer that includes a dilator, the guide being adapted to receive the dilator of the introducer, the introducer being adapted to receive the cut catheter; and placing in position of the introducer by means of the guide in the body of the patient.

19. The preparation method according to claim 15, wherein when the guide is in the desired position, the distal end of the guide is located at the junction of the superior vena cava and the right atrium of the patient.

20. The preparation method according to claim 15, wherein the determination of the position of the distal end of the guide in the body of the patient includes an electrocardiogram measurement, a modification of the wave P measured during the electrocardiogram indicating the positioning if the guide in the desired position.

\* \* \* \* \*